United States Patent
Corvari et al.

(10) Patent No.: US 11,918,623 B2
(45) Date of Patent: *Mar. 5, 2024

(54) GIP/GLP1 AGONIST COMPOSITIONS

(71) Applicant: Eli Lilly and Company, Indianapolis, IN (US)

(72) Inventors: Vincent John Corvari, Carmel, IN (US); Christopher Sears Minie, Zionsville, IN (US); Dinesh Shyamdeo Mishra, Carmel, IN (US); Ken Kangyi Qian, Carmel, IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 17/741,067

(22) Filed: May 10, 2022

(65) Prior Publication Data

US 2022/0273762 A1 Sep. 1, 2022

Related U.S. Application Data

(63) Continuation-in-part of application No. 16/441,329, filed on Jun. 14, 2019, now Pat. No. 11,357,820.

(60) Provisional application No. 62/688,632, filed on Jun. 22, 2018.

(51) Int. Cl.
*A61K 38/00* (2006.01)
*A61K 9/00* (2006.01)
*A61K 38/16* (2006.01)
*A61K 47/02* (2006.01)
*A61K 47/10* (2017.01)
*A61M 5/20* (2006.01)

(52) U.S. Cl.
CPC ............ *A61K 38/16* (2013.01); *A61K 9/0019* (2013.01); *A61K 47/02* (2013.01); *A61K 47/10* (2013.01); *A61M 5/20* (2013.01)

(58) Field of Classification Search
None
See application file for complete search history.

(56) References Cited

U.S. PATENT DOCUMENTS

| | | | |
|---|---|---|---|
| 7,084,243 B2 | 8/2006 | Glaesner et al. | |
| 7,498,308 B2 | 3/2009 | Glaesner et al. | |
| 8,114,833 B2* | 2/2012 | Pedersen | A61P 3/04 |
| | | | 530/308 |
| 8,734,394 B2* | 5/2014 | Adams | A61M 5/326 |
| | | | 604/242 |
| 9,474,780 B2* | 10/2016 | Bokvist | A61K 38/16 |
| 11,357,820 B2* | 6/2022 | Corvari | A61K 38/16 |
| 2009/0232807 A1 | 9/2009 | Glaesner et al. | |
| 2010/0196405 A1 | 8/2010 | Ng | |
| 2012/0329708 A1 | 12/2012 | DiMarchi et al. | |

FOREIGN PATENT DOCUMENTS

WO 2011094337 8/2011

OTHER PUBLICATIONS

Fransson, J., & Espander-Jansson, A. (1996). Local tolerance of subcutaneous injections. *Journal of pharmacy and pharmacology*, 48(10), 1012-1015.

Williamson, A.;Hoggart,(2005)Pain: A review of three commonly used pain rating scales. *Journal of Clinical Nursing*, 14, (7), 798-804).

Millican, R.L., et al., Diabetes, Suppl., Abstract Book, A363 1504-P, 65th Scientific Sessions, NY col. 54 (Jun. 2005).

Laursen, T., Hansen, B., & Fisker, S. (2006). Pain perception after subcutaneous injections of media containing different buffers. *Basic & clinical pharmacology & toxicology*, 98(2), 218-221.

Troy, Editor, (2006) *Remington: The Science and Practice of Pharmacy* (21st edition Lippincott Williams & Wilkins) https://books.google.com/books?isbn=0781746736.

Saha, J. K., Xia, J., Millican, R., Grondin, J. M., Glaesner, W., & Jakubowski, J. A. (2007). DPP-4 Resistant Glucagon-Like Peptide-1 Analog LY548806: A Novel Agent for Control of Acute Hyperglycemia.

\* cited by examiner

*Primary Examiner* — Aradhana Sasan
*Assistant Examiner* — Mercy H Sabila
(74) *Attorney, Agent, or Firm* — MaCharri Vorndran-Jones

(57) ABSTRACT

A composition of tirzepatide, comprising an agent selected from NaCl and propylene glycol; and dibasic sodium phosphate is provided.

15 Claims, No Drawings

Specification includes a Sequence Listing.

SEQUENCE LISTING

```
<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is nonnaturally occurring
      amino acid 2-Aminoisobutyric Acid
<220> FEATURE:
<221> NAME/KEY: MISC_FEATURE
<222> LOCATION: (13)..(13)
<223> OTHER INFORMATION: Xaa at position 13 is nonnaturally occurring
      amino acid 2-Aminoisobutyric Acid
<220> FEATURE:
<221> NAME/KEY: MOD_RES
<222> LOCATION: (20)..(20)
<223> OTHER INFORMATION: Lys at position 20 is chemically modified
      through conjugation to the epsilon-amino group of the K side-chain
      with (2-[2-(2-Amino-ethoxy)-ethoxy]-acetyl)2-(gamma-Glu)1-CO-
      (CH2)18-CO2H
<220> FEATURE:
<221> NAME/KEY: MOD_RES
<222> LOCATION: (39)..(39)
<223> OTHER INFORMATION: Ser at position 39 is amidated as a C-terminal
      primary amide

<400> SEQUENCE: 1

Tyr Xaa Glu Gly Thr Phe Thr Ser Asp Tyr Ser Ile Xaa Leu Asp Lys
1               5                   10                  15

Ile Ala Gln Lys Ala Phe Val Gln Trp Leu Ile Ala Gly Gly Pro Ser
            20                  25                  30

Ser Gly Ala Pro Pro Pro Ser
        35
```

GIP/GLP1 AGONIST COMPOSITIONS

This application is a divisional application of U.S. application Ser. No. 16/411,329, filed on Jun. 14, 2019, which claims priority to U.S. Provisional Application No. 62/688,632, filed on Jun. 22, 2018. The disclosure of each of the above applications is incorporated herein by reference in its entirety.

REFERENCE TO AN ELECTRONIC SEQUENCE LISTING

The sequence listing is entitled "Sequence Listing" and is associated with the enclosed application, entitled "GIP/GLP1 AGONIST COMPOSITIONS." The sequence listing was created on Jun. 22, 2018 and submitted with U.S. 62/688,632. The contents of the electronic sequence listing are herein incorporated by reference in their entirety.

The present invention is a pharmaceutical GIP/GLP1 co-agonist peptide composition for subcutaneous injection. The composition comprises tirzepatide, NaCl, and dibasic sodium phosphate. The composition provides commercially acceptable shelf-life stability, in-use stability, and is associated with acceptable patient injection site experience. An alternative composition comprises tirzepatide, propylene glycol, and dibasic sodium phosphate that also provides acceptable shelf-life stability.

Diabetes mellitus is a chronic disorder characterized by hyperglycemia resulting from defects in insulin secretion, insulin action, or both. In type 2 diabetes mellitus ("T2D"), the combined effects of impaired insulin secretion and insulin resistance are associated with elevated blood glucose levels. Tirzepatide is a GIP/GLP1 co-agonist peptide useful in the treatment of diabetes. Tirzepatide is useful in the treatment of obesity.

U.S. Pat. No. 9,474,780 generally describes compositions containing a GIP/GLP1 agonist, administered by parenteral routes. U.S. Pat. No. 9,474,780 describes and claims tirzepatide. There is a desire for compositions of tirzepatide providing acceptable stability and acceptable patient injection site experience.

The present invention seeks to meet these needs by providing pharmaceutically-acceptable compositions of tirzepatide, or a pharmaceutically acceptable salt thereof; comprising an agent selected from the group consisting of NaCl and propylene glycol; and dibasic sodium phosphate.

In an embodiment, the agent is NaCl. In an embodiment, the NaCl concentration is from about 6.2 mg/mL to about 9.5 mg/mL. In an embodiment the NaCl concentration is from about 7.0 mg/mL to about 9.0 mg/mL. In an embodiment, the NaCl concentration is about 8.2 mg/mL.

In an embodiment, the agent is propylene glycol. In an embodiment, the propylene glycol concentration is from about 12.0 mg/mL to about 18.0 mg/mL. In an embodiment the propylene glycol concentration is from about 14.0 mg/mL to about 16.0 mg/mL. In an embodiment, the propylene glycol concentration is about 15.0 mg/mL.

In an embodiment, the dibasic sodium phosphate concentration is from about 0.67 mg/mL to about 2.68 mg/mL. In an embodiment, the dibasic sodium phosphate is about 1.0 mg/mL to about 3.0 mg/mL. In an embodiment, the dibasic sodium phosphate is about 1.34 mg/mL.

In an embodiment, the tirzepatide concentration is from about 5 mg/mL to about 30 mg/mL and the agent is NaCl. In an embodiment, the tirzepatide concentration is from about 10 mg/mL to about 30 mg/mL. In an embodiment, the tirzepatide concentration is from about 5 mg/mL to about 30 mg/mL; the NaCl concentration is about 8.2 mg/mL, and dibasic sodium phosphate concentration is from about 0.67 mg/mL to about 2.68 mg/mL. In an embodiment, the tirzepatide concentration is from about 5 mg/mL to about 30 mg/mL; the NaCl concentration is about 8.2 mg/mL, dibasic sodium phosphate concentration is from about 0.67 mg/mL to about 2.68 mg/mL, and the composition is presented in a single use automatic injection apparatus.

In an embodiment, the tirzepatide concentration is from about 5 mg/mL to about 30 mg/mL; and the agent is propylene glycol. In an embodiment, the tirzepatide is from about 5 mg/mL to about 30 mg/mL; the propylene glycol is from about 12.0 mg/mL to about 18.0 mg/mL, and the dibasic sodium phosphate concentration is about 1.34 mg/mL. In an embodiment, the tirzepatide concentration is from about 5 mg/mL to about 30 mg/mL; the propylene glycol is about 15.0 mg/mL, and the dibasic sodium phosphate concentration is about 1.34 mg/mL.

In an embodiment, the tirzepatide concentration is from about 5 mg/mL to about 30 mg/mL. In certain embodiments, the tirzepatide concentration is from about 10 mg/mL to about 30 mg/mL. In an embodiment the tirzepatide concentration is selected from the group consisting of 5, 10, 15, 20, 25, and 30 mg/mL. In an embodiment, 0.5 mL or less of the composition is administered as a dose. In an embodiment, the tirzepatide concentration is selected from the group consisting of 10, 20, and 30 mg/mL.

In an embodiment, the tirzepatide composition further comprises a preservative. In an embodiment, the tirzepatide composition comprises tirzepatide, dibasic sodium phosphate, propylene glycol, and a preservative. In an embodiment, the preservative is selected from the group consisting of metacresol and phenol. In an embodiment, the metacresol concentration is from about 2.0 mg/mL to about 4.0 mg/mL. In an embodiment the metacresol concentration is from about 3.0 mg/mL to about 3.5 mg/mL. In an embodiment, the metacresol concentration is about 3.15 mg/mL. In an embodiment, the phenol concentration is from about 3.0 mg/mL to about 7.0 mg/mL. In an embodiment the phenol concentration is from about 4.0 mg/mL to about 6.0 mg/mL. In an embodiment, the phenol concentration is about 5.0 mg/mL. In an embodiment, a tirzepatide composition is provided wherein tirzepatide concentration is from about 5 mg/mL to about 30 mg/mL; propylene glycol concentration is from about 12.0 mg/mL to about 18.0 mg/mL; dibasic sodium phosphate concentration is from about 0.67 to about 2.68 mg/mL; and metacresol concentration is from about 2.0 mg/mL to about 4.0 mg/mL. In an embodiment, the metacresol concentration is about 3.15 mg/mL. In an embodiment, a tirzepatide composition is provided wherein tirzepatide concentration is from about 5 mg/mL to about 30 mg/mL; propylene glycol concentration is from about 12.0 mg/mL to about 18.0 mg/mL; dibasic sodium phosphate concentration is from about 0.67 to about 2.68 mg/mL; and phenol concentration is from about 3.0 mg/mL to about 7.0 mg/mL. In an embodiment, a tirzepatide composition is provided wherein tirzepatide concentration is from about 5 mg/mL to about 30 mg/mL; propylene glycol concentration is from about 12.0 mg/mL to about 18.0 mg/mL; dibasic sodium phosphate concentration is from about 0.67 to about 2.68 mg/mL; and phenol concentration is about 5.0 mg/mL.

In an embodiment, the dose of a tirzepatide composition is administered about once weekly. In an embodiment, the dose of a tirzepatide composition is administered once every seven days.

In an embodiment, there is provided a method of treating diabetes comprising administering to a human in need thereof an effective dose of one of the above-described compositions.

In an embodiment, there is provided a method of treating obesity comprising administering to a human in need thereof an effective dose of one of the above-described compositions. In an embodiment, there is provided a method of providing therapeutic weight loss comprising administering to a human in need thereof an effective dose of one of the above-described compositions. In an embodiment, there is provided a method of treating a condition mediated by GIP/GLP1 co-agonist activity comprising administering to a human in need thereof an effective dose of one of the above-described compositions.

In an embodiment, there is provided one of the above-described compositions for use as a medicament.

In an embodiment, there is provided one of the above-described compositions for use in the treatment of diabetes. In an embodiment, there is provided one of the above-described compositions for use in the treatment of obesity.

In an embodiment, there is provided one of the above-described compositions for use in providing therapeutic weight loss. In an embodiment, there is provided one of the above-described compositions for use in providing non-therapeutic weight loss.

According to another aspect of the present invention, there is provided an article of manufacture comprising one of the above-described compositions. In certain embodiments, the article of manufacture is a multi-use vial. In certain embodiments, the article of manufacture is a pre-filled syringe. In certain embodiments, the article of manufacture is an automatic injection apparatus ("auto-injector"). An example of an auto-injector, as contemplated herein, is presented in U.S. Pat. No. 8,734,394.

As used herein, "tirzepatide" means a GIP/GLP1 co-agonist peptide as described in U.S. Pat. No. 9,474,780 and described by CAS Registry Number: 2023788-19-2. Tirzepatide is described in Example 1 of U.S. Pat. No. 9,474,780, with the following sequence: YX$_1$EGTFTSDYSIX$_2$LDKIAQKAFVQWLIAGGPSSGAPPPS wherein X$_1$ is Aib; X$_2$ is Aib; K at position 20 is chemically modified through conjugation to the epsilon-amino group of the K side-chain with (2-[2-(2-Amino-ethoxy)-ethoxy]-acetyl)$_2$-($\gamma$Glu)$_1$-CO—(CH$_2$)$_{18}$—CO$_2$H; and the C-terminal amino acid is amidated as a C-terminal primary amide (SEQ ID NO: 1).

When used herein, "pharmaceutically acceptable salt" is well known to the skilled artisan. In an embodiment is a pharmaceutically acceptable salt that is a tirzepatide trifluoroacetate salt.

When used herein, the term "does not contain a surfactant" means that the composition contains no added surfactant agents, or contains only a de minimis quantity of an added surfactant.

When used herein the term "propylene glycol" is well known to the skilled artisan. Propylene glycol is also represented by the formula: $C_3H_8O_2$.

The compositions of the present invention have concentrations of tirzepatide 30 between 5 mg/mL and 30 mg/mL. The compositions of the present invention are likely to have specific concentrations of 5, 10, 15, 20, 25, and 30 mg/mL. Such compositions may be presented in a pre-filled syringe. Such pre-filled syringe may be useful for administering one half milliliter of such composition per patient per dose. A dose of tirzepatide composition may be administered using a dosing schedule determined by a physician.

The compositions are sterile when first produced. If provided in a multi-use vial or cartridge, an anti-microbial preservative compound or mixture of compounds that is compatible with the other components of the composition may be added at sufficient strength to meet applicable regulatory anti-microbial preservative requirements. Pharmaceutically acceptable preservatives are well-known in the art. (See, e.g., Remington: The Science and Practice of Pharmacy (D. B. Troy, Editor, 21$^{st}$ Edition, Lippincott, Williams & Wilkins, 2006). In an embodiment, the preservative is meta-cresol. In an embodiment, the preservative is phenol. A composition for single use pre-filled syringe requires no preservative. In an embodiment, the composition does not contain a surfactant.

The pH of tirzepatide compositions of the present invention is typically 6.5 to 7.5 and it is adjusted using physiologically appropriate acids and bases, as may be required to achieve the desired pH. In an embodiment, the pH target is between 6.7 and 7.3. Patient injection site experience is a consideration for a subcutaneously administered composition. It is desirable to select a composition associated with an acceptable patient injection site experience. For example, NaCl and citrate have been associated with painful stinging at the injection site. (Laursen, T.; Hansen, B.; Fisker, S. Pain perception after subcutaneous injections of media containing different buffers. *Basic & Clinical Pharmacology & Toxicology* 2006, 98, (2), 218-221), (Fransson, J.; Espander-Jansson, A. Local tolerance of subcutaneous injections. *Journal of Pharmacy and Pharmacology* 1996, 48, (10), 1012-1015.) It is further desirable to match the tonicity (i.e., osmolality) of body fluids at the injection site as closely as possible when administering the compositions because solutions that are not approximately isotonic with body fluids can produce a painful stinging sensation when administered. It is desirable that the compositions be approximately isotonic with body fluids at the sites of injection. The present composition comprising tirzepatide, NaCl, and dibasic sodium phosphate is associated acceptable patient injection site experience. Likewise, the composition comprising tirzepatide, propylene glycol, and dibasic sodium phosphate is associated with acceptable patient injection site experience.

In an embodiment, the pH is adjusted using a base to facilitate dissolution in the buffer solution. The addition of an acid to the composition may be required to adjust the pH to the desired pH range. In an embodiment, NaOH is used to facilitate dissolution of tirzepatide in a buffer. In an embodiment, HCl is added to adjust the pH of the composition containing the dissolved tirzepatide to the desired pH range.

The compositions of the present invention are typically administered subcutaneously. The compositions are typically administered using a pre-filled, disposable pen, reusable pen, or automatic pen injector. The composition may be administered using a multi-use vial or a pump device. In an embodiment, the device is an automatic injection apparatus as claimed by U.S. Pat. No. 8,734,394.

A composition comprising tirzepatide, NaCl, and dibasic sodium phosphate provides a desired shelf life stability and provides patients with an acceptable injection site experience. Likewise, a composition comprising tirzepatide, propylene glycol, and dibasic sodium phosphate provides a desired shelf life stability and provides patients with an acceptable injection site experience. As used herein, "shelf life stability" is measured under controlled conditions at about 5 degrees Celsius. A composition comprising tirzepatide, NaCl, and dibasic sodium phosphate provides acceptable in-use stability. Likewise, a composition comprising tirzepatide, propylene glycol, and dibasic sodium phosphate provides acceptable in-use stability. As used herein, the term "in-use stability" refers to the stability of the composition measured under controlled conditions at or about 25 degrees Celsius or at or about 40 degrees Celsius.

EXAMPLE #1—COMPOSITION CONTAINING NACL

The composition is prepared substantially as described herein. The compositions containing 5, 10, 15, 20, 15, and 30 mg/mL of tirzepatide each contain the ingredients set forth in Table 1. Acid or base is optionally added to attain the desired pH range. Water is added quantum satis (q.s.) to one milliliter total final volume.

TABLE 1

Formulation of Tirzepatide, Phosphate, and NaCl

| Ingredient | Concentration (mg/mL) |
| --- | --- |
| Tirzepatide | 5, 10, 15, 20, 25, and 30 |
| dibasic sodium phosphate* | 1.34 |
| NaCl | 8.2 |

*5 mM. phosphate buffer is used

EXAMPLE #2—COMPOSITION CONTAINING PROPYLENE GLYCOL

The composition is prepared substantially as described herein. The compositions providing 5, 10, 15, 20, 15, and 30 mg/mL compositions of tirzepatide each contain the ingredients set forth in Table 2. Acid or base is optionally added to attain the desired pH range. Water is added quantum satis to one milliliter total final volume.

TABLE 2

Formulation of Tirzepatide, Phosphate, and Propylene Glycol

| Ingredient | Concentration (mg/mL) |
| --- | --- |
| Tirzepatide | 5, 10, 15, 20, 25, and 30 |
| dibasic sodium phosphate* | 1.34 |
| Propylene glycol | 15 |

*5 mM phosphate buffer is used

Size Exclusion Chromatography (SEC) In-Use Stability Study

This procedure is an isocratic size exclusion HPLC method with UV detection at 214 nm and is designed to determine the relative amounts of tirzepatide monomer and total aggregates. Monomer and aggregates are reported as peak area percent to the total area. The procedure is stability indicating as measured by its ability to resolve known impurities from tirzepatide. This study compares alternate compositions with the compositions of this invention, prepared as shown by Table 3. The stability from this study is shown in Table 4.

TABLE 3

Stability study comparing alternate compositions:

| Ingredient | Formulation | | | |
| --- | --- | --- | --- | --- |
|  | Control | NaCl | Mannitol | Glycerol |
| Tirzepatide (mg/mL) | 2 | 2 | 2 | 2 |
| Sodium phosphate dibasic 7H$_2$O (mg/mL)** | 2.68 | 2.68 | 2.68 | 2.68 |
| NaCl (mg/mL) | — | 8.8 | — | — |
| Mannitol (mg/mL) | — | — | 45 | — |
| Glycerol (mg/mL) | — | — | — | 27 |
| Water (mg/mL) | q.s. to 1 mL | q.s. to 1 mL | q.s. to 1 mL | q.s. to 1 mL |

**10 mM phosphate buffer is used

TABLE 4

Tirzepatide monomer (% peak area) by size-exclusion chromatography (SEC)

| Composition | Temp (° C.) | Time (month) | | | |
| --- | --- | --- | --- | --- | --- |
| | | 0 | 0.5 | 1 | 2 |
| Control (Table 3) | 25 | 98.25 | 98.15 | 97.76 | 96.63 |
|  | 40 |  | 97.62 | 95.80 | 93.19 |
| NaCl (Table 3) | 25 | 98.23 | 98.13 | 97.95 | 97.47 |
|  | 40 |  | 97.84 | 97.28 | 96.22 |
| Mannitol (Table 3) | 25 | 98.23 | 97.87 | 97.39 | 95.17 |
|  | 40 |  | 96.72 | 92.71 | 83.48 |
| Glycerol (Table 3) | 25 | 98.25 | 98.11 | 97.77 | 96.62 |
|  | 40 |  | 97.36 | 94.51 | 84.11 |

Shelf Life Stability Study

RP-HPLC:

This procedure is a gradient reversed-phase HPLC method with UV detection at 214 nm and is designed to determine the quantity, identity, and purity of tirzepatide in the drug product. Identity is determined by matching the retention time of the main peak with that of the main peak of an external reference standard. Quantity is determined by the comparison of the main peak area with the corresponding peak in the external reference standard. Impurities and related substances are reported as peak area percent to the total peak area. The procedure is stability indicating as judged by its ability to resolve known impurities from tirzepatide. As shown by Table 4, a composition comprising NaCl as a tonicity agent provides acceptable in-use stability.

Size Exclusion Chromatography (SEC) Shelf-Life Stability Study

The size exclusion stability study methods and RP-HPLC described herein above are applied to compare compositions comprising NaCl as a tonicity and stabilizing agent with compositions comprising propylene glycol as a tonicity and stabilizing agent. This study illustrates the acceptable shelf-life stability of a composition of this invention comprising NaCl agent or comprising propylene glycol as agent. The compositions used for this study are set forth in Table 5. The stability from this study is shown in Table 6.

TABLE 5

Comparison between NaCl and propylene glycol

| Ingredient | Formulation of NaCl as agent | Formulation of Propylene glycol as agent |
|---|---|---|
| Tirzepatide (mg/mL) | 20 | 20 |
| Sodium phosphate dibasic 7H$_2$O (mg/mL)* | 1.34 | 1.34 |
| NaCl (mg/mL)) | 8.8 | — |
| Propylene glycol (mg/mL) | — | 15 |
| Water | q.s. to mL | q.s. to mL |

*5 mM phosphate buffer is used in the study

TABLE 6

Comparison of NaCl to Propylene Glycol as an agent in Tirzepatide formulations by determining monomer (% peak area) by SEC and purity by RP-HPLC

| Composition | Temp (° C.) | Time (month) 0 | 1 | 2 | 3 |
|---|---|---|---|---|---|
| Monomer by SEC | | | | | |
| NaCl (Table 5) | 5 | 99.35 | — | — | 98.81 |
|  | 30 |  | 97.20 | 98.03 | 97.79 |
| Propylene glycol (Table 5) | 5 | 98.51 | 98.20 |  |  |
|  | 30 |  | 97.94 |  |  |
| Purity by RP-HPLC | | | | | |
| NaCl (Table 5) | 5 | 92.87 | — | — | 95.95 |
|  | 30 |  | 91.70 | 90.40 | 89.26 |
| Propylene glycol (Table 5) | 5 | 93.38 | 93.31 |  |  |
|  | 30 |  | 92.04 |  |  |

Pain Upon Injection Study:

All compositions are prepared as described by Table 7. Each solution composition vial is held at room temperature about 30 minutes, but not more than four hours. Reconstituted lyophilized compositions are used immediately. All injections are rotated between the 4 quadrants of the abdomen, in the following order; lower left quadrant; lower right quadrant; upper left quadrant; and upper right quadrant. A syringe with a 29 gauge needle is used to administer the composition from a vial. A fold of skin at the injection site is grasped by the subject, and the needle is inserted at about a 45 degree angle. A second person uses a stop watch to measure the length of time of injection. The subject slowly pushes the plunger of the syringe all the way until 0.5 mL of the composition is injected. The target time of injection is 4 seconds duration, and not more than 5 seconds. The needle is removed from the skin after injection and skin is released from the subject's grasp. The subject immediately assesses the pain after each injection. Pain measurements are assessed using a 100-mm validated visual analog scale (VAS) for pain. The VAS is a well-validated tool to assess injection-site pain (Williamson, A.; Hoggart, B. Pain: A review of three commonly used pain rating scales. *Journal of Clinical Nursing* 2005, 14, (7), 798-804). The VAS is presented as a 10-cm (100-mm) line, anchored by verbal descriptors, usually "no pain" and "worst imaginable pain." The subject is asked to mark the 100-mm line to indicate pain intensity at time points and as clinically indicated. A staff member uses a caliper to measure the distance from 0 to the mark that the subject placed on the VAS, and to record the measurement in the source document. Results from this study appear in Table 8. An acceptable patient injection site experience is reflected by a mild pain intensity indication (compared to moderate or severe).

TABLE 7

| Compositions for Pain Intensity Study. Ingredient | Formulation of NaCl | Formulation of Propylene glycol |
|---|---|---|
| Tirzepatide (mg/mL) | 20 | 20 |
| Sodium phosphate dibasic 7H$_2$O (mg/mL)* | 1.34 | 1.34 |
| NaCl (mg/mL)) | 8.8 | — |
| Propylene glycol (mg/mL) | — | 15 |
| Water | q.s. to mL | q.s. to mL |

| Ingredient | Placebo of NaCl as agent | Placebo of Propylene glycol as agent |
|---|---|---|
| Tirzepatide (mg/mL) | 0 | 0 |
| Sodium phosphate dibasic 7H$_2$O (mg/mL)* | 1.34 | 1.34 |
| NaCl (mg/mL)) | 8.8 | — |
| Propylene glycol (mg/mL) | — | 15 |
| Water | q.s. to mL | q.s. to mL |

| Ingredient | Formulation of NaCl as agent-Lyophylized |
|---|---|
| Tirzepatide (mg/mL) | 20 |
| Sodium phosphate dibasic 7H$_2$O (mg/mL)* | 1.34 |
| NaCl (mg/mL)) | 8.8 |
| Propylene glycol (mg/mL) | — |
| Water: sterile water for injection- reconstitute; swirl to dissolve | q.s. to mL |

*5 mM phosphate buffer is used in the study

TABLE 8

VAS pain score.

| Composition (per Table 7) | Pain intensity Mild (VAS: 0 mm-30 mm) | Moderate (VAS: 31 mm-70 mm) | Severe (VAS: 71 mm-100 mm) |
|---|---|---|---|
| Tirzepatide lyophilized, reconstituted | 90% | 5% | 5% |
| Tirzepatide composition propylene glycol | 100% | 0% | 0% |
| Tirzepatide composition NaCl | 100% | 0% | 0% |
| Placebo composition NaCl | 100% | 0% | 0% |
| Placebo composition propylene glycol | 100% | 0% | 0% |

Sequences

SEQ ID NO:1

Tirzepatide

YX$_1$EGTFTSDYSIX$_2$LDKIAQKAFVQWLIAGGPSSGAPPPS wherein X$_1$ is Aib; X$_2$ is Aib; K at position 20 is chemically modified through conjugation to the epsilon-amino group of the K side-chain with (2-[2-(2-Amino-ethoxy)-ethoxy]-acetyl)$_2$-(γGlu)$_1$-CO—(CH$_2$)$_{18}$—CO$_2$H; and the C-terminal amino acid is amidated as a C-terminal primary amide

We claim:

1. A method of treating obesity comprising administering to a human in need thereof an effective dose of a pharmaceutical composition comprising tirzepatide, or pharmaceutically acceptable salt thereof, wherein the tirzepatide concentration is from about 5 mg/mL to about 30 mg/mL; dibasic sodium phosphate is from about 0.67 to about 2.68 mg/mL; NaCl at a concentration from about 6.2 mg/mL to about 9.5 mg/mL; and optionally comprising from about 3.0 mg/mL to about 7.0 mg/mL phenol.

2. A method of treating obesity as claimed by claim 1 wherein the dose is administered using an automatic injection apparatus.

3. A method of treating obesity as claimed by claim 2 wherein the dose is administered once weekly.

4. A method of treating obesity comprising administering to a human in need thereof an effective dose of a pharmaceutical composition comprising tirzepatide, or a pharmaceutically acceptable salt thereof;
   NaCl at a concentration from about 6.2 mg/mL to about 9.5 mg/mL; and
   dibasic sodium phosphate.

5. A method as claimed by claim 4, wherein the tirzepatide, or a pharmaceutically acceptable salt thereof, concentration is from about 5 mg/mL to about 30 mg/mL.

6. A method as claimed by claim 5 wherein the dibasic sodium phosphate concentration is from about 1 mg/mL to about 3 mg/mL.

7. A method as claimed by claim 4 wherein the dibasic sodium phosphate concentration is from about 0.67 mg/mL to about 2.68 mg/mL.

8. A method as claimed by claim 7 wherein the dibasic sodium phosphate concentration is about 1.34 mg/mL.

9. A method as claimed by claim 8 wherein the tirzepatide, or a pharmaceutically acceptable salt thereof, concentration is selected from the group consisting of 5, 10, 15, 20, 25, and 30 mg/mL.

10. A method as claimed by claim 9 wherein the NaCl concentration is from about 7.0 mg/mL to about 9.0 mg/mL.

11. A method as claimed by claim 10 wherein the NaCl concentration is about 8.2 mg/mL.

12. A method as claimed by claim 1 wherein the tirzepatide, or a pharmaceutically acceptable salt thereof, concentration is selected from the group consisting of 5, 10, 15, 20, 25, and 30 mg/mL.

13. A method as claimed by claim 12 wherein the NaCl concentration is from about 7.0 mg/mL to about 9.0 mg/mL.

14. A method as claimed by claim 13 wherein the NaCl concentration is about 8.2 mg/mL.

15. A method of treating obesity comprising administering to a human in need thereof an effective dose of a pharmaceutical composition comprising:
   (a) tirzepatide, or pharmaceutically acceptable salt thereof, wherein the tirzepatide concentration is from about 5 mg/mL to about 30 mg/mL;
   (b) dibasic sodium phosphate, wherein the dibasic sodium phosphate concentration is about 1.34 mg/mL; and (c) NaCl, wherein the NaCl concentration is about 8.2 mg/mL; and wherein the dose is administered using an automatic injection apparatus.

* * * * *

UNITED STATES PATENT AND TRADEMARK OFFICE
CERTIFICATE OF CORRECTION

PATENT NO. : 11,918,623 B2
APPLICATION NO. : 17/741067
DATED : March 5, 2024
INVENTOR(S) : Vincent John Corvari et al.

It is certified that error appears in the above-identified patent and that said Letters Patent is hereby corrected as shown below:

On the Title Page
Column 1, Line 1: In the Related U.S. Application Data, "Continuation-in-part" should read --Continuation--
Column 2, Line 4: In Other Publications, "A.;Hoggart," should read --A.; Hoggart,--
Column 2, Line 6: In Other Publications, "804)" should read --804.--.

In the Specification
Column 1, Line 3: "divisional" should read --continuation--
Column 1, Line 3: "16/411,329," should read --16/441,329,--

Signed and Sealed this
Nineteenth Day of November, 2024

Katherine Kelly Vidal
*Director of the United States Patent and Trademark Office*